United States Patent
Matov et al.

(10) Patent No.: US 9,375,300 B2
(45) Date of Patent: Jun. 28, 2016

(54) IDENTIFYING FORCES ON A TOOTH

(75) Inventors: Vadim Matov, San Jose, CA (US); Igor Faradjev, Campbell, CA (US); Bastien Pesenti, Santa Clara, CA (US); Sergey Geyn, Rula (RU); Konstantin Tenzin, Moscow Region (RU)

(73) Assignee: Align Technology, Inc., San Jose, CA (US)

( * ) Notice: Subject to any disclaimer, the term of this patent is extended or adjusted under 35 U.S.C. 154(b) by 127 days.

(21) Appl. No.: 13/365,167

(22) Filed: Feb. 2, 2012

(65) Prior Publication Data
US 2013/0204583 A1   Aug. 8, 2013

(51) Int. Cl.
*A61C 3/00*     (2006.01)
*A61C 19/04*    (2006.01)
*A61C 7/00*     (2006.01)
*A61C 7/08*     (2006.01)

(52) U.S. Cl.
CPC ............... *A61C 19/04* (2013.01); *A61C 7/002* (2013.01); *A61C 7/08* (2013.01)

(58) Field of Classification Search
CPC .......... A61C 19/04; A61C 7/002; A61C 7/08; A61C 7/00; G06F 17/50
USPC ................................................. 433/24; 703/1
See application file for complete search history.

(56) References Cited

U.S. PATENT DOCUMENTS

| | | | | |
|---|---|---|---|---|
| 5,447,432 A * | 9/1995 | Andreiko et al. | 433/24 |
| 5,533,895 A * | 7/1996 | Andreiko et al. | 433/24 |
| 5,879,158 A * | 3/1999 | Doyle et al. | 433/24 |
| 5,975,893 A * | 11/1999 | Chishti et al. | 433/6 |
| 6,210,162 B1 * | 4/2001 | Chishti et al. | 433/213 |
| 6,227,850 B1 * | 5/2001 | Chishti et al. | 433/24 |
| 6,406,292 B1 * | 6/2002 | Chishti et al. | 433/24 |
| 6,471,511 B1 | 10/2002 | Chishti et al. | |
| 6,682,346 B2 | 1/2004 | Chishti et al. | |
| 6,739,870 B2 * | 5/2004 | Lai et al. | 433/24 |
| 6,802,713 B1 | 10/2004 | Chishti et al. | |
| 7,134,874 B2 * | 11/2006 | Chishti et al. | 433/24 |
| 7,229,282 B2 * | 6/2007 | Andreiko et al. | 433/24 |
| 7,320,592 B2 | 1/2008 | Chishti et al. | |
| 7,543,511 B2 | 6/2009 | Kimura et al. | |
| 7,641,473 B2 * | 1/2010 | Sporbert et al. | 433/24 |
| 7,869,983 B2 * | 1/2011 | Raby et al. | 703/2 |
| 7,874,837 B2 | 1/2011 | Chishti et al. | |
| 7,905,725 B2 * | 3/2011 | Chishti et al. | 433/24 |
| 7,972,134 B2 * | 7/2011 | Lai et al. | 433/24 |
| 8,029,277 B2 * | 10/2011 | Imgrund et al. | 433/24 |
| 8,075,306 B2 * | 12/2011 | Kitching et al. | 433/24 |
| 2001/0002310 A1 * | 5/2001 | Chishti et al. | 433/24 |
| 2004/0152036 A1 * | 8/2004 | Abolfathi | 433/24 |
| 2004/0161722 A1 * | 8/2004 | Lai et al. | 433/24 |
| 2004/0197728 A1 * | 10/2004 | Abolfathi et al. | 433/24 |
| 2005/0244791 A1 * | 11/2005 | Davis et al. | 433/213 |

(Continued)

*Primary Examiner* — Cris L Rodriguez
*Assistant Examiner* — Mirayda A Aponte
(74) *Attorney, Agent, or Firm* — Brooks, Cameron & Huebsch, PLLC

(57) ABSTRACT

The present disclosure includes computing device related, systems, and methods for identifying force placed on a tooth are described herein. One method includes receiving initial orthodontic data (IOD) including teeth data; creating a virtual set of teeth from the IOD; receiving dental appliance information including at least one of dental appliance material properties and characteristics; virtually placing a dental appliance, formed from the dental appliance information, onto the virtual set of teeth; and determining one or more forces applied to the teeth based on information from the IOD and dental appliance information.

20 Claims, 7 Drawing Sheets

(56) References Cited

U.S. PATENT DOCUMENTS

| | | | |
|---|---|---|---|
| 2006/0257815 A1* | 11/2006 | De Dominicis | 433/24 |
| 2007/0212659 A1* | 9/2007 | Andreiko et al. | 433/24 |
| 2008/0182220 A1* | 7/2008 | Chishti et al. | 433/24 |
| 2008/0268400 A1* | 10/2008 | Moss et al. | 433/24 |
| 2009/0191502 A1 | 7/2009 | Cao et al. | |
| 2009/0191503 A1 | 7/2009 | Matov et al. | |
| 2010/0028825 A1* | 2/2010 | Lemchen | 433/24 |
| 2010/0138025 A1 | 6/2010 | Morton et al. | |

\* cited by examiner

IDENTIFYING FORCES ON A TOOTH

TECHNICAL FIELD

The present disclosure relates to systems and methods for virtually identifying forces placed on teeth.

BACKGROUND

Many dental treatments involve repositioning misaligned teeth and changing bite configurations for improved cosmetic appearance and dental function. Orthodontic repositioning can be accomplished, for example, by applying controlled forces to one or more teeth over a period of time.

An example of orthodontic repositioning that can occur through a dental process uses one or more positioning dental appliances, such as aligners, for realigning teeth. Placement of an appliance over the teeth can provide controlled forces in specific locations to gradually move the teeth into a new configuration. Repetition of this process with successive appliances in progressive configurations can move the teeth through a series of intermediate arrangements to a final desired arrangement.

Typically, in order to design each aligner, the progression of the teeth from an initial position to a final position is determined, via a computing device. This progression is then segmented into a plurality of segments and an aligner is formed that is based upon each of the positions of the teeth at those segments.

Currently, a treatment plan is designed by beginning with a current teeth configuration, proposing an end configuration, generating, via a computing device, a path for the teeth from the current configuration to the end configuration, and segmenting that path into multiple segments and forming the appliances based on the data from each of these segments.

Each appliance may then be sequentially placed on a patient's teeth with the theory that the dental appliance will act on the teeth to move each tooth in a particular direction toward its position of the next progressive segment. However, in some instances, the appliance does not move the teeth to the position of the next progressive segment for a number of reasons, as discussed below. Accordingly, in these instances, the treatment plan then has to be revised and new aligners created to remedy the different than anticipated positioning of one or more of the teeth.

DETAILED DESCRIPTION

Figure 1A:
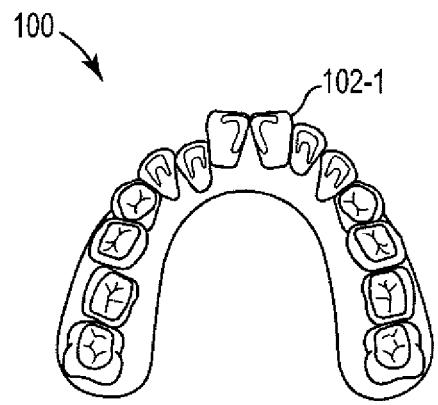
FIG. 1A illustrates an initial virtual dental model according to one or more embodiments of the present disclosure.

Embodiments of the present disclosure include computing device related, system, and method embodiments for virtually testing force placed on a tooth are described herein. For example, one or more embodiments include a method of virtually identifying force placed on a tooth. Some such methods can include, for example, receiving initial orthodontic data (IOD) including teeth data, creating a virtual set of teeth from the IOD, receiving dental appliance information including at least one of dental appliance material properties and characteristics, virtually placing a dental appliance, formed from the dental appliance information, onto the virtual set of teeth, and determining one or more forces applied to the teeth based on information from the IOD and dental appliance information.

One or more embodiments can virtually place a dental appliance with cavity geometry of the first stage of the treatment plan over the IOD and identifying actual forces applied to the teeth contained in the IOD by the dental appliance. One or more embodiments can include determining desired forces to be applied by the dental appliance to move the teeth to the first stage teeth positions, and designing optimized dental appliance cavity geometry and/or position to reach the desired forces to move teeth to the next stage teeth positions based on the dental appliance material properties, characteristics, and shape of teeth.

Embodiments of the present disclosure can be utilized in the design of dental appliance products for use in the mouth of a patient, such as anchors and other attachments and potentially to aligner surfaces (e.g., dimples, ridges, thickness, shape, orientation, etc.), material properties, and their interaction with the teeth. Embodiments can allow a user to identify the forces present on a set of teeth on one jaw of the mouth or on both jaws (e.g., as tooth and/or appliance surfaces on opposing jaws interact with each other).

Various embodiments can be beneficial in determining how much force to apply to each tooth and the teeth as a whole and components of force from what one or more directions and/or types (e.g., linear, torsional, etc). This information can be, for example, used to determine the shape and/or positioning of the dental appliance or other item for the movement of teeth to get closest to the force and/or direction desired for moving the teeth.

For example, at present, a dental appliance (e.g., an attachment or aligner) having an already designed shape may be placed on a patient's tooth or teeth with the theory that the dental appliance will act on the tooth to move it in a particular direction. However, this theory is typically part of a treatment plan selected, based upon experience with the type of dental appliance, by a treatment professional and the actual result, based on the actual forces at work including those from other teeth and other dental appliances and/or other items being utilized for the movement of the teeth, may result in a different orientation than expected. This can, therefore, result in more, less, or different movement to achieve the desired result.

Accordingly, the forces acting on the teeth and their movements have not previously been considered in the analysis of the appliance configurations. Through use of the embodiments of the present disclosure, it may be possible to shape the appliances based on force which may, for example, reduce the number of treatments or movements and/or reduce the amount of force used, which may result in less treatment time and/or reduced patient discomfort, among other benefits.

Embodiments of the present disclosure can allow the user to virtually test the shape and/or placement of an attachment and/or other appliance structure with the perspective of its effect on multiple teeth (e.g., the whole set of teeth on the jaw). Embodiments can also make adjustments to the shape and/or placement and/or retry the movement until the best or most satisfactory result is achieved.

In some embodiments, initial orthodontic data (IOD), for example, from an actual patient's mouth, typodont data, and/or scanned appliance data can be obtained and the forces, desired during a portion of a treatment plan to move a tooth from one position to another, can be determined. The use of actual case data (e.g., from a particular current patient's mouth or a prior patient's mouth) can be used, for example, where a dental appliance may be desired to perform a particular movement with respect to a particular tooth positioning due to a particular malocclusion.

Treatment plan case data can be analyzed to determine the movement of a particular tooth from one position to a subsequent position based upon the movements of the other teeth and/or other structures in the patient's mouth. This information can then be utilized, for example, in an embodiment's analysis of forces with respect to one or more proposed attachments and/or other aligner related movement analysis.

Embodiments of the present disclosure can provide a user interface where a virtual model of the teeth is presented in three dimensions. Once the forces and moments of the forces are determined (e.g., through use of IOD and/or dental appliance data), they can be presented on the user interface (e.g., they can be presented as vector arrows showing direction and/or magnitude of desired force) among other information about the force that may be helpful to the user.

These forces can, for example, include forces from any dental appliances on the tooth, forces from neighboring teeth, gingival forces applied and/or modified for effects from other teeth on the set and their forces and/or movements, forces from bone structures and/or other forces that may affect the tooth. Some embodiments can utilize appliance wall thickness and/or feature data (e.g., data about features such as dimples, reinforcement structures). This information can, for example, be measured based on an actual appliance, measurements taken from a virtual model, and/or estimated based upon thickness sampling of measurements taken from previous appliances.

In some instances, it can be this combination of forces (some forces can be additive, neutral, or subtractive to each other) that may be difficult to ascertain without use of embodiments of the present disclosure. Accordingly, embodiments of the present disclosure can more accurately estimate the forces that are to be used. In some instances, such analysis could move a tooth more directly to a targeted location and avoid additional movements that might be need if the analysis was not done. In some embodiments, a greater or lesser force can be determined to be used to begin tooth movement and therefore, the treatment can be more effective.

In some embodiments, the force can be quantified with respect to a single point, such as the center of mass or the center of rotation, associated with a tooth or can be associated with one or more contact surfaces of a tooth (e.g., contact with other teeth or contact with the appliance).

Embodiments of the present disclosure can include many tools for the creation and alteration of the dental appliances or other items related to the movement of the tooth. These items can include one or more libraries of tooth shapes and treatment plan data (e.g., orthodontic data such as typodonts, actual patient tooth data, and/or treatment plan data), dental appliance shapes, data regarding mounting materials that could be used, and/or data regarding other characteristics of a dental appliance or tooth or mouth structure that may be beneficial in determining a force.

Some embodiments also include editing tools to change the shape of the dental appliances or other items related to the movement of the tooth. For example, suitable tools could include those typically provided with respect to drafting and/or computer aided design software applications.

In some embodiments, the desired forces and the actual forces can be illustrated on the virtual model so that the user can see the differences between the actual and desired forces (e.g., force and/or magnitude vectors for both the desired and actual forces). This can be helpful, for example, by allowing the user to see the differences and adjust the shape or position of the dental appliance or other item related to the movement of the tooth.

The actual force can then be recalculated and then illustrated to show the revised force of the revised shape and/or position, in some embodiments. The resulting effect can be shown on the other teeth of the set in some embodiments, which may help the user identify any incidental issues with a proposed treatment plan or dental appliance position and/or shape.

In some embodiments, multiple calculated positions and/or shapes can be illustrated (e.g., the forces generated from a first position and a second position can be illustrated together and, in some instances, with the desired forces). This can be beneficial, for example, to identify how the change from a first to a second position affected the forces. It can also be beneficial to identify if the change from a first to a second position is adjusting the forces created closer to those of the desired forces, among other benefits.

Embodiments can, for example, utilize Discrete Differential Geometry for its calculations versus other systems using Finite Element Analysis. The can be beneficial, for example because, such embodiments can do calculations much quicker and/or with less computing time and/or resources, in many instances.

Various embodiments, can be used to determine what the resulting configuration of teeth would be based upon the appliance proposed in the treatment plan. This can be beneficial, for example, to determine whether the appliance proposed would move the tooth as desired, if another type of appliance should be used, or if the appliance should be redesigned to provide the desired movement of the tooth.

Some embodiments can identify if the appliance will stretch and where such stretching will occur. This can be beneficial, for example, to identify points in which the appliance should be reinforced to reduce or eliminate the stretching.

One proposed method includes: receive initial orthodontic data (IOD) of teeth of a patient, identify a virtual target dental model of the teeth based on the IOD representing a treatment plan, identify one or more virtually created dental appliances utilized in the treatment plan, compute one or more desired force parameters of a dental appliance to achieve a final position of a particular segment of the treatment plan, and estimate actual forces generated by the virtually created dental appliance as applied to one or more teeth and verify the virtually created dental appliance is applying a desired force parameter to the one or more teeth.

Another method includes the following elements: receiving initial orthodontic data (IOD) of teeth, receiving desired tooth positions of a treatment plan for the teeth contained in the IOD, computing a desired force and a desired torque to be applied to the teeth to reach the desired tooth positions, and designing an optimized dental appliance shape and position to move teeth to the desired tooth positions.

Embodiments of the present disclosure can also be beneficial for reasons including, utilizing real world force information, tooth data, and/or other structural data to calculate the position for placement and/or potential shape of an dental appliance or other appliance feature and/or general shaping of an appliance without actually having to test all of these iterations in an actual patient or group of patients.

In the following section of the detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that process, electrical, or mechanical changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 208 may reference element "8" in FIG. 2, and a similar element may be referenced as 408 in FIG. 4.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense. As used herein, "a number of" something can refer to one or more such things.

Although the overarching term "orthodontics" is used herein, the present disclosure may relate to treatments of an orthognathic nature. For example, in cases including treatment of a patient's underlying skeletal structure, teeth may be rearranged by surgically repositioning underlying bones that hold the teeth in order to achieve a desired final bite arrangement. In both orthodontic and orthognathic treatment approaches, alignment of the teeth may be evaluated pre-, mid-, and/or post-treatment.

Treatment professionals typically select a treatment plan for a patient's teeth based upon experience with certain types of physical features and/or dental appliances to be used. An assumption is often made that the dental appliance will move the teeth or a certain tooth in a particular direction based on the shape of the dental appliance.

However, an actual result based on the actual forces at work may result in a different orientation than expected, which may be an undesired result. With the use of computing device executable instructions, a treatment professional can establish a custom treatment target specific to each tooth or a set of teeth for each individual patient. With this treatment target in mind, a force applied to a tooth by a dental appliance can be virtually identified and tested.

Virtual dental models from a scan of a patient's dentition can be provided with computer-aided design and/or manufacturing systems, including tooth-treatment systems. An initial orthodontic data (IOD) representing an initial tooth arrangement may be obtained in a variety of ways.

For example, the patient's teeth may be imaged to obtain digital data using direct and/or indirect structured light, X-rays, three-dimensional X-rays, lasers, destructive scanning, computer-aided tomographic images or data, magnetic resonance images, intra-oral scanning technology, photographic reconstruction, and/or other imaging techniques. The IOD can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the IOD. The data produced by the range acquisition system may be converted to other formats to be compatible with the software which is used for manipulating images within the data, as described herein.

Referring now to FIG. 1A, there is illustrated an initial virtual dental model 100 according to one or more embodiments of the present disclosure. As described herein, the initial virtual dental model 100 can be obtained from a first scan of a patient dentition prior to treatment or at an intermediate state of treatment (e.g., before treatment has been completed) or the final scan of a certain treatment phase. One or more embodiments of the present disclosure include receiving a virtual IOD and a desired position of a tooth contained in the virtual IOD. The initial virtual dental model (e.g., virtual IOD) can also include a model of an individual tooth (e.g., tooth 102-1) that is part of a full dental model, such as full virtual dental model 100.

Figure 1B:
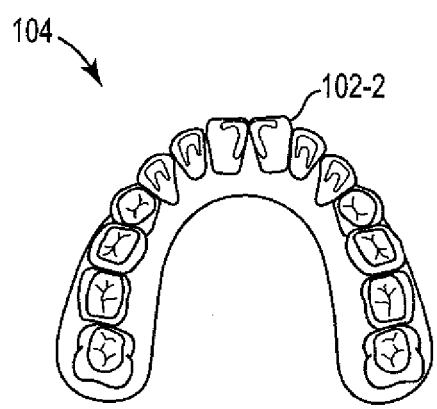
FIG. 1B illustrates a target virtual dental model corresponding to the initial virtual dental model illustrated in FIG. 1A according to the present disclosure.

FIG. 1B illustrates a target virtual dental model 104. The target virtual dental model 104 can be created by modifying the initial virtual dental model 100 according to one or more treatment goals of a treatment plan. The one or more treatment goals can be case-specific (e.g., specific to the particular patient on which the initial virtual dental model 100 was based). The target virtual dental model 104 can also include a target model of an individual tooth (e.g., tooth 102-2) that is part of a full dental model similar to full target dental model 104. In some embodiments, the virtual IOD 100 and the target virtual dental model 104 can be displayed via a user interface in three dimensions.

Treatment plans are designed by beginning with a current teeth configuration (e.g., the virtual IOD 100), determining the target virtual dental model 104, generating a path for the teeth from the virtual IOD to the target configuration, and segmenting that path into multiple segments to form the appliances. Embodiments of the present disclosure can virtually identify and test the force applied to teeth by a designed appliance or physical feature can be used to determine what the actual resulting configuration of teeth would be based upon the aligner proposed in the treatment plan versus the intended configuration.

In some embodiments, these forces can include forces from any dental appliances on the tooth, forces from neighboring teeth, gingival forces applied and modified based on effects from other teeth on the set and their forces and/or movements, forces from bone structures and/or other forces that may affect the tooth. In some embodiments, the appliance wall thickness and feature data (e.g., dimples, reinforcement structures, shape, orientation with respect to one or more teeth, etc) can be used to determine the actual resulting configuration of teeth versus the intended configuration. The force information can be measured based on an actual appliance and/or estimated based upon thickness sampling of measurements taken from other appliances that have been previously measured.

Virtually identifying and/or testing forces can be utilized in the optimization for products for use in the mouth of a patient, such as aligners, anchors, attachments, and other dental appliances, and potentially to appliance surfaces (e.g., dimples, ridges, thickness, shape, orientation, etc.), appliance material properties, and their interaction with the teeth. Virtually identifying and testing one or more applied forces allows a user to identify the forces present on a set of teeth from a dental appliance and to optimize the dental appliance shape and/or position such that desired forces are acting on the teeth to move teeth along a particular segment of the treatment plan.

Virtually testing an applied force to a tooth can also be beneficial in determining how much force to apply to the tooth and from what one or more directions. This information can be used to determine the shape and/or positioning of the dental appliance to get closest to the necessary force and/or direction desired for moving the tooth.

Figure 2:
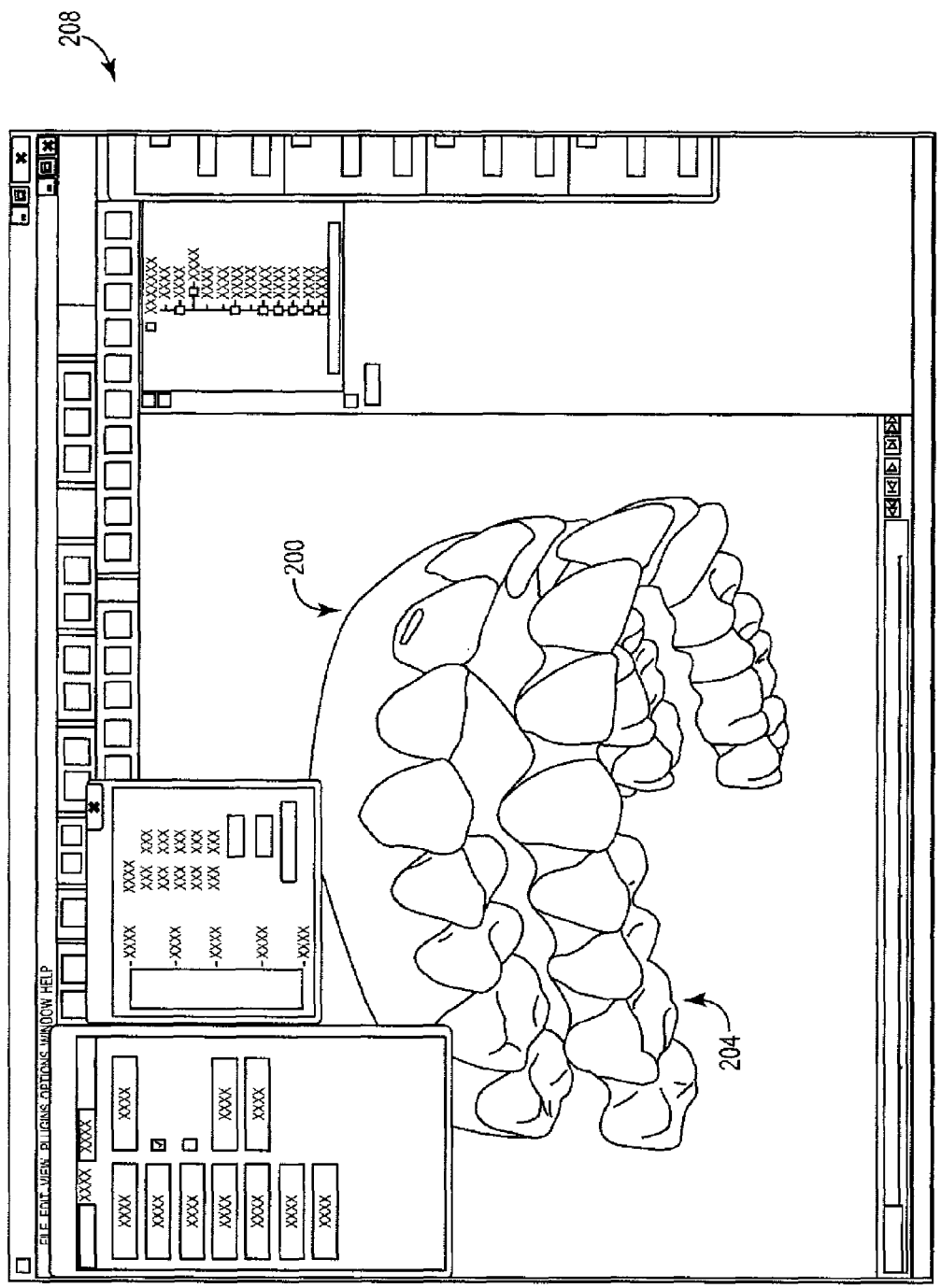
FIG. 2 illustrates an example of an initial virtual dental model, a dental appliance, and an example of a user interface according to one or more embodiments of the present disclosure.

FIG. 2 illustrates an example three-dimensional model of teeth (e.g., the IOD 200), an appliance 204, and an example of a user interface 208 for identifying force placed on the teeth 200 according to one or more embodiments of the present disclosure. The model of teeth can be the IOD 200 or can be a position of the teeth in a particular tooth path segment of the treatment plan (e.g., position subsequent to the starting position of the treatment plan). For example, each tooth path segment of the treatment plan can have corresponding dental appliances or appliance configured to move the teeth from a subsequent position of the tooth path segment to another position closer to a final position of the treatment plan.

In one or more embodiments, a user can virtually place the dental appliance 204 with, for example, a cavity geometry of the first stage of the treatment plan over the IOD 200 and identify actual forces applied to the teeth contained in the IOD 200 from the dental appliance 204 based on the dental appliance material properties, characteristics, and/or shape of the teeth.

For example, the elastic deformation of the dental appliance based on the appliance material properties, characteristics, and shape of teeth can determine an amount of stress on the appliance, a force and/or torque applied to each tooth, and/or individual contacts of the aligner on teeth and their relative strength. Knowing the forces acting on the dental appliance and on the teeth allows a user to more accurately create the dental appliance characteristics to most efficiently move the teeth from an initial position to a final position of the treatment plan corresponding to a dental appliance.

Figure 3:
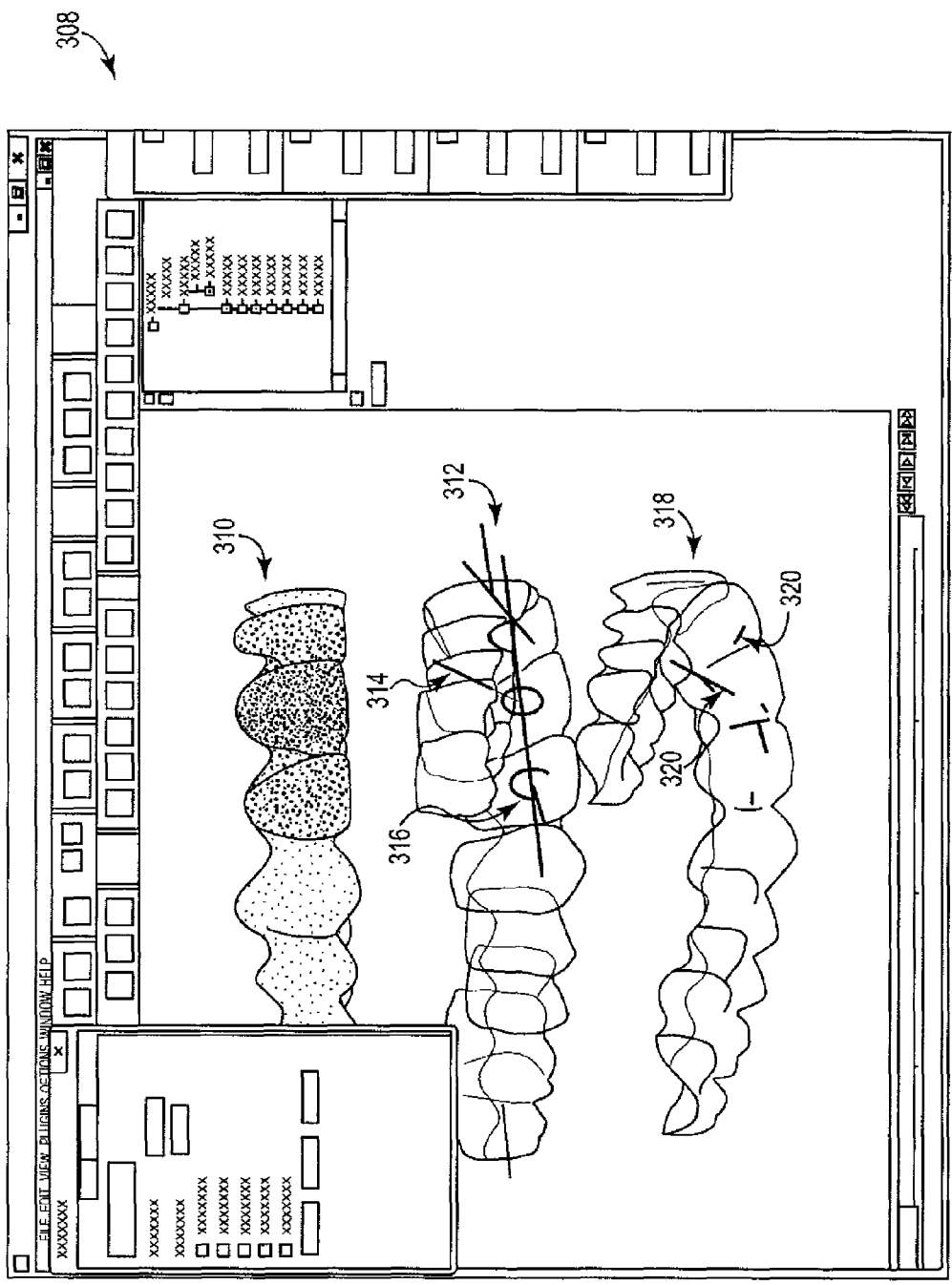
FIG. 3 illustrates an example of virtual three-dimensional dental appliances with identified forces and an example of a user interface according to one or more embodiments of the present disclosure.

FIG. 3 illustrates examples of three-dimensional dental appliances and an example of a user interface 308 for identifying force on the dental appliance and applied to the virtual set of teeth (e.g., the IOD 200 in FIG. 2) according to one or more embodiments of the present disclosure. In one or more embodiments, a user can virtually identify force placed on the dental appliance and to the teeth when the dental appliance is placed over the IOD.

As seen in FIG. 3, there are three three-dimensional dental appliances displayed on the user interface 308. The first dental appliance 310 illustrates an amount of internal stress acting on the dental appliance when placed on the IOD. The amount of stress is indicated as a light number of dots to a heavier number of dots scale. For example, areas of the dental appliance 310 that have a low amount of stress are displayed as a light number of dots, whereas areas of the dental appliance 310 having higher amounts of stress are displayed as heavier number of dots.

The second dental appliance 312 in the user interface 308 illustrates a force and torque applied to each tooth. Vectors 314 can represent the force applied to a tooth by the dental appliance. Additionally, the vectors 316 can represent the torque applied to the teeth from the dental appliances. The vectors can represent the force, the torque, and/or the magnitude of each.

The third dental appliance 318 in the user interface 308 illustrates individual contacts of the dental appliance on the teeth and the relative strength of the contact. For example, arrows 320 can illustrate the direction and the magnitude of the local force where the dental appliance contacts the teeth.

By identifying the actual forces acting on the dental appliance and on the teeth, the dental appliance and features of the dental appliance may be editable by a user such that the actual forces are sufficiently similar to desired forces as discussed further herein.

Figure 4:
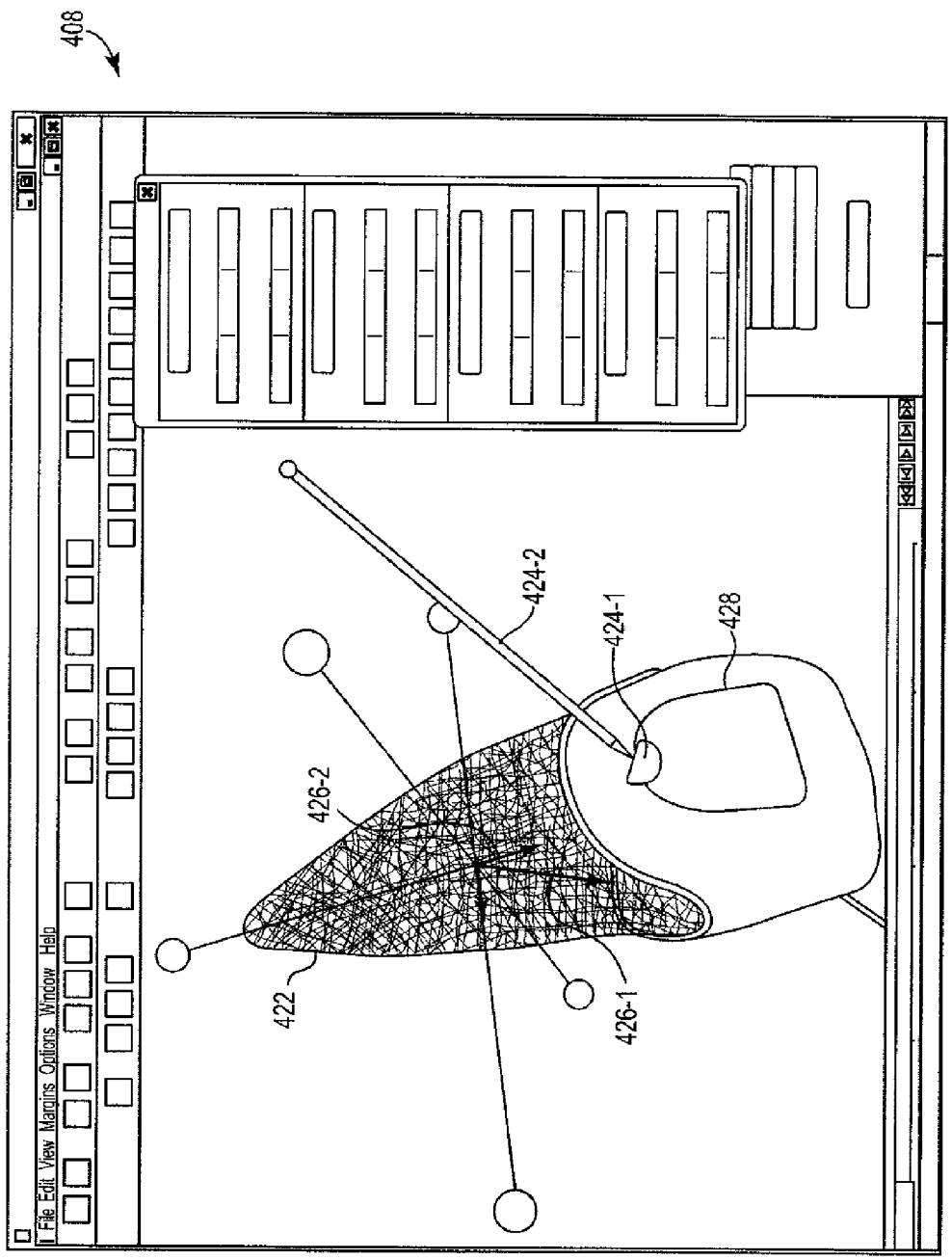
FIG. 4 illustrates an example virtual three-dimensional tooth model and an example of a user interface for identifying force placed on a tooth according to one or more embodiments of the present disclosure.

For one or more embodiments, once the actual forces of the dental appliance on the tooth are identified, one or more desired forces to be applied by the dental appliance to move the teeth to the first stage teeth positions are determined. FIG. 4 illustrates an example three-dimensional tooth model and an example of a user interface 408 for determining desired force and torque placed on a tooth 422 according to one or more embodiments of the present disclosure.

In one or more embodiments, a user can virtually test the shape and/or placement of a dental appliance or other appliance structure (e.g., physical feature 421-1) and make adjustments to the shape or placement and retry the movement until the best or most satisfactory result is achieved.

The model of tooth 422 includes arrows 426-1 and 426-2 representing a desired force and torque components for movement of tooth 422. For example, arrows 426-1 and 426-2 can represent an ideal force and torque components for movement.

The model of tooth 422 also includes tooth surface feature 424-1 (e.g., dental appliance, dimple, etc.) and an arrow 424-2 that can represent a desired feature force direction and/or magnitude, given a set of physical and/or appliance characteristics. A feature or features (e.g., feature 424-1) can apply a force and/or torque to the tooth 422, which can be represented by arrow 424-2.

A possible location 428 where a feature 424-1 can be placed on tooth 422 can also be available on the tooth model and user interface 408. The tooth, as well as features of the dental appliance may be editable by a user as further discussed herein.

For one or more embodiments, once the desired forces for moving one or more teeth are identified, an aligner cavity geometry and/or position to reach the desired forces can be optimized to move the teeth to the desired teeth positions based on the dental appliance material properties, characteristics, and shape of teeth. Designing optimized aligner cavity geometry and/or position can include virtually testing and adjusting the dental appliance iteratively to reach the desired forces for moving the teeth to the first stage teeth location.

Figure 5:
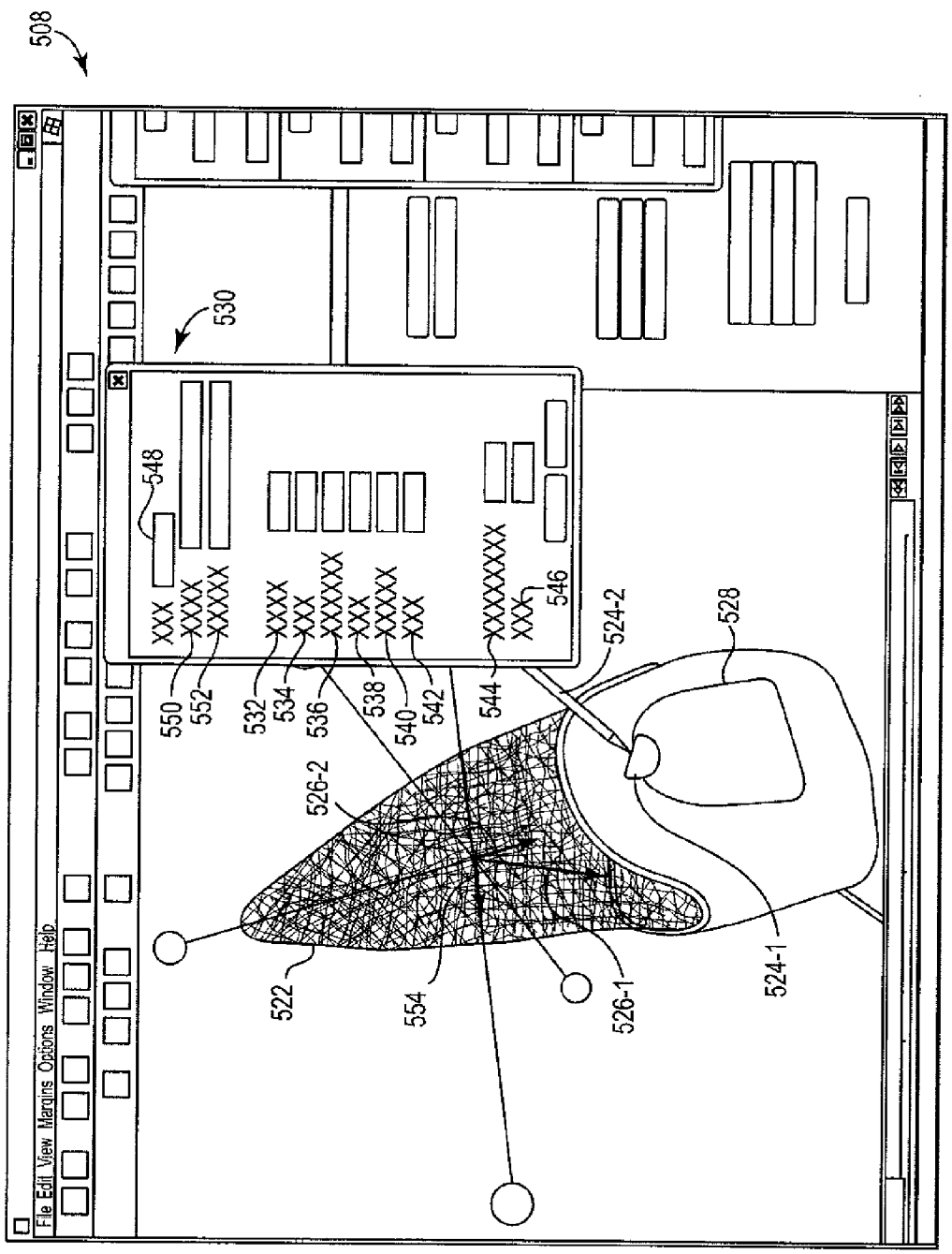
FIG. 5 illustrates an example virtual three-dimensional tooth model and an example of a user interface for identifying force placed on a tooth according to one or more embodiments of the present disclosure.

FIG. 5 illustrates an example three-dimensional tooth model and an example of a user interface 508 for testing force placed on a tooth 522 according to one or more embodiments of the present disclosure. In some embodiments, a user can take data from an actual patient's mouth or a typodont and determine the forces desired during a portion of a treatment plan to move a tooth from one position to another. A typodont can refer to a virtual dental model including a number of ideal tooth shapes (e.g., from a reference library of idealized tooth shapes).

The use of actual case data may be useful, for example, where a dental appliance may be desired to perform a particular movement with respect to a particular tooth positioning due to a particular malocclusion. In some embodiments, a user can enter physical parameters of a dental appliance (e.g., appliance, aligner, dimple, etc.) to be created or altered into a location and orientation window 530.

For example, a user can enter such parameters as a length 532, a width 534, a prominence 536, a depth 538 of inside tooth 522, an activation angle 540, and an activator offset on inactive surfaces 542. In some embodiments, the system can be configured to allow a user to other settings, such as an iso-surface gradient width 544 and a voxel size 546. In various embodiments, a user can choose to identify tooth 522 by a number or some other identifier and enter or choose the identifier in a drop-down box such as box 548. A user can also choose to enter parameters for a center of the dental appliance and an active surface (e.g., parameters 550 and 552).

In some embodiments, a user interface (e.g., user interface 508) is provided where a virtual model of the tooth is presented in three dimensions. Once the forces and moments of the forces on the tooth are determined, they can be presented on the user interface (e.g., they can be presented as vector arrows showing direction and/or magnitude of desired force or stress) among other information about the force that may be helpful to the user.

Vector arrows 526-1 and 526-2 can represent desired (e.g., ideal) force and/or torque for movement of tooth 522, and vector arrow 554 can represent a force and torque applied to tooth 522 by a feature 524-1. Vector arrow 524-2 can represent a desired (e.g., optimal) feature force direction and magnitude, given a set of features (e.g., dental appliance, dimple, etc).

Treatment plan case data can be analyzed to determine the movement of a particular tooth from a first position e.g., initial position or intermediate position that is prior to the subsequent position) to a subsequent (e.g., desired) position. This information can then be utilized in an analysis of forces with respect to proposed dental appliances or other aligner related movement analysis.

Tools for the creation and/or alteration of the dental appliances or other items related to the movement of the tooth can be utilized to virtually test force placed on a tooth in some embodiments. These items can include one or more libraries of tooth shapes and treatment plan data (e.g., typodonts, actual patient tooth data, and/or treatment plan data), dental appliance shapes, data regarding mounting materials that could be used, and/or data regarding other characteristics of an aligner, tooth, and/or mouth structure.

The items can also include editing tools to change the shape of the dental appliances or other items related to the movement of the tooth. For example, suitable tools could include those typically provided with respect to drafting and/or computer aided design software applications.

As discussed, in some embodiments, the desired forces and the actual forces can be illustrated on the virtual model so that the user can see the differences between the actual and desired forces (e.g., force and/or magnitude vectors for both the desired and actual forces). This can be helpful, for example, by allowing the user to see the differences and adjust the shape or position of the dental appliance or other item related to the movement of the tooth. The actual force can then be recalculated and/or illustrated to show the revised force of the revised shape and/or position.

Also as discussed above, in some embodiments, multiple calculated positions and/or shapes can be illustrated (e.g., the forces generated from a first position and a second position can be illustrated together and, in some instances, with the desired forces). This can be beneficial, for example, to identify how the change from a first to a second position affected the forces. It can also be beneficial to identify if the change from a first to a second position is adjusting the forces created closer to those of the desired forces.

It should be noted that one force that may be quantified for movement of the tooth is for total movement of the tooth from a first position to a second position. However, forces from the gingiva and bone interactions for some force calculations can also be incorporated and, therefore, in some embodiments, forces for different stages of movement can be determined, such as initial force needed for bone breakdown versus force needed for movement once the bone restructuring has occurred. For example, in some embodiments, the movement from a first position to a second position may be determined by calculating the force sufficient to enable the tooth to begin to move (e.g., the first and second positions could be relatively close or adjacent and therefore the force to create that movement would be the force needed to begin moving the tooth).

Modeling techniques involving gingival or bone structures can, for example, be accomplished by modeling the root structure and/or the structure of the jaw bone and/or gingiva. This can, for instance, be accomplished using patient data and/or typodont data.

In some embodiments, a center of mass can be calculated for the tooth, and the forces (e.g., desired forces) can be associated with the center of mass. In some embodiments, a center of rotation can be calculated, and the forces can be associated with the center of rotation.

In some embodiments, a possible placement area 528 in which an attachment can be positioned on a tooth can be identified. This information can be obtained through experiential data programmed into the software and/or entered by the user or multiple users. Additionally, this can be calculated based upon the forces that are to be generated.

For example, in some embodiments, the forces generated can be determined for an attachment that has been selected by the user for placement on the tooth and a possible placement area 528 can be identified for the placement of the attachment on the tooth. The possible placement area 528 can, for example, be based upon where the placement of the attachment would result in a certain result that would be within a threshold proximity to the desired result. In some embodiments, as the shape and/or orientation of the dental appliance is changed, the possible placement area can be recalculated.

The possible placement area 528 could, for instance, be based on areas where attachment could actually be achieved (e.g., portions of the tooth where an attachment would be sufficiently adhered to the tooth so that it does not come detached or obstructed by a structure such as a tooth surface not being shaped for attachment thereto or too far below the gingiva). This calculation could be determined through experiential data or based upon one or more characteristics of the tooth, and/or materials to be used (e.g., adhesion characteristics of the tooth surface, adhesion characteristics of the adhesion material, adhesion characteristics of the dental appliance material, shape of the adhesion surface of the attachment, and/or shape of the surface of the tooth, etc).

For example, the possible placement area 528 may not include the edge areas, overly curved surfaces, and/or contoured surfaces of the tooth because adhesion to those surfaces may be difficult, in some situations. It may not be reasonable to use some areas of the tooth, as certain areas would not properly associate or connect with a surface of an appliance, and as such, in some embodiments, association information and/or surface information can be used in determining possible placement areas.

For example, improper association can include, for instance, an appliance position that is calculated to be undesirably close to or in contact with a neighboring tooth, an appliance position that negatively impacts a neighboring tooth and/or area surrounding the possible placement area, a position that would not provide proper fit between the attachment and another appliance such as an aligner, and/or negatively impacting the area around an aligner and/or the appliance, among others. Improper connection with a surface of an appliance can include, for instance, can include not having a tooth surface that would provide a secure bonding surface for attachment of an appliance thereon, among others.

In some embodiments, the possible placement area 528 may by "dynamic" in that it can change as certain criteria (e.g., the shape and/or type of appliance, bonding material, material of the appliance, etc.) changes. For example, an attachment of a particular shape may have more preferable results when placed on a first area of a tooth than a second attachment having a second shape, perhaps, with a different surface shape on the surface to be bonded to the surface of the tooth and therefore, the possible placement area can be changed so that the user interface can indicate the changes to a user.

As discussed herein, in one or more embodiments, a user can virtually place a dental appliance such as an appliance over the IOD to identify forces acting on the appliance. For example, identifying forces acting on the appliance can determine if the appliance will relax and where such relaxation will occur. This can be beneficial, for example, to identify points in which the appliance should be reinforced to reduce or eliminate the relaxation.

Figure 6:
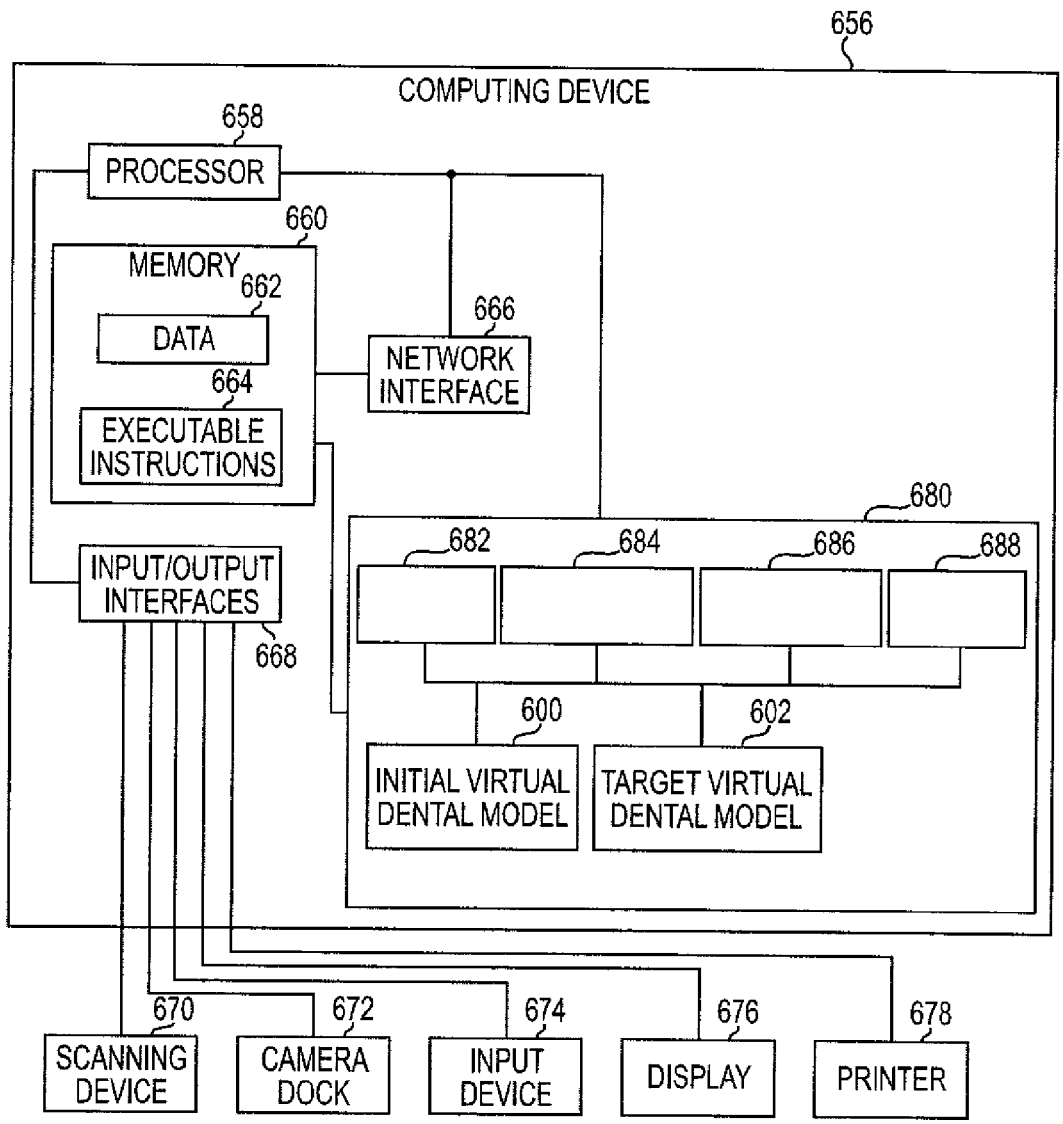
FIG. 6 illustrates a system for virtually identifying force placed on a tooth according to one or more embodiments of the present disclosure.

FIG. 6 illustrates a system for virtually identifying force placed on a tooth according to one or more embodiments of the present disclosure. In the system illustrated in FIG. 6, the system includes a computing device 656 having a number of components coupled thereto. The computing device 656 includes a processor 658 and memory 660. The memory 660 can include various types of information including data 662 and executable instructions 664 discussed herein.

Memory and/or the processor may be located on the computing device 656 or off the device in some embodiments. As such, as illustrated in the embodiment of FIG. 6, a system can include a network interface 666. Such an interface can allow for processing on another networked computing device or such devices can be used to obtain information about the patient or executable instructions for use with various embodiments provided herein.

As illustrated in the embodiment of FIG. 6, a system can include one or more input and/or output interfaces 668. Such interfaces can be used to connect the computing device with one or more input or output devices.

For example, in the embodiment illustrated in FIG. 6, the system can include connectivity to a scanning device 670, a camera dock 672, an input device 674 (e.g., a keyboard, mouse, etc.), a display device 676 (e.g., a monitor), a printer 678, and one or more other input devices. The input/output interface 668 can receive data, storable in the data storage device (e.g., memory 660), representing a digital dental model of a patient's dentition.

In some embodiments, the scanning device 670 can be configured to scan one or more physical molds of a patient's dentition. In one or more embodiments, the scanning device 670 can be configured to scan the patient's dentition directly. The scanning device 670 can be configured to input data to the application modules 680.

The camera dock 672 can receive an input from an imaging device (e.g., a two-dimensional imaging device) such as a digital camera or a printed photograph scanner. The input from the imaging device can be stored in the data storage device (e.g., memory 660).

The processor 658 can be configured to provide a visual indication of a virtual dental model on the display 676 (e.g., on a GUI running on the processor 658 and visible on the display 676). The GUI can be configured to allow a treatment professional or other user to input treatment goals, to create a target virtual dental model 602, and/or enter desired or actual dental appliance parameters. Input received via the GUI can be sent to the processor 658 as data and/or can be stored in memory 660.

Such connectivity can allow for the input and/or output of data and/or instructions among other types of information. Although some embodiments may be distributed among various computing devices within one or more networks, such systems as illustrated in FIG. 6 can be beneficial in allowing for the capture, calculation, and/or analysis of information discussed herein.

The processor 658, in association with the data storage device (e.g., memory 660), can be associated with data and/or application modules 680. The processor 658, in association with the memory 660, can store and/or utilize data and/or execute instructions to provide a number of application modules for virtually testing force placed on a tooth.

Such data can include the initial virtual dental model 600 and the target virtual dental model 602. Such application modules can include a creation module 682, a verification module 684, an identification module 686, and/or a display module 688.

The computation module 684 can be configured to compute a desired position, a desired orientation, and a desired relative magnitude of point contact force of a dental appliance to achieve the target virtual dental model 602. Additionally, the computation module can determine a desired force that is present on the dental appliance based on the dental appliance material properties, characteristics, and shape of teeth.

The creation module 682 can be configured to virtually create a dental appliance based on a treatment plan. For example, the creation module 682 can create a plurality of dental appliances, such as appliances, that are configured to move teeth from the initial virtual dental model 600 to the target virtual dental model 602, where each appliance is configured to move the teeth a portion of the path from the initial dental model 600 to the target virtual dental model 602. In some embodiments, a single dental appliance can be used to move the teeth to the target virtual dental model 602.

The identification module 686 can be configured to identify actual forces present on the created dental appliance and on the teeth and verify the dental appliance is applying the desired force parameters to the teeth contained in the initial virtual dental model. For example, the identification module 686 can test the virtually created dental appliance and verify it has the desired position, orientation, relative magnitude of point contact force, a desired amount of stress, and desired individual contacts of the dental appliance.

The display module 688 can be configured to display the virtually created dental appliance and the point contact force. The display module 688 can be configured to display the information on display device 676.

Figure 7:
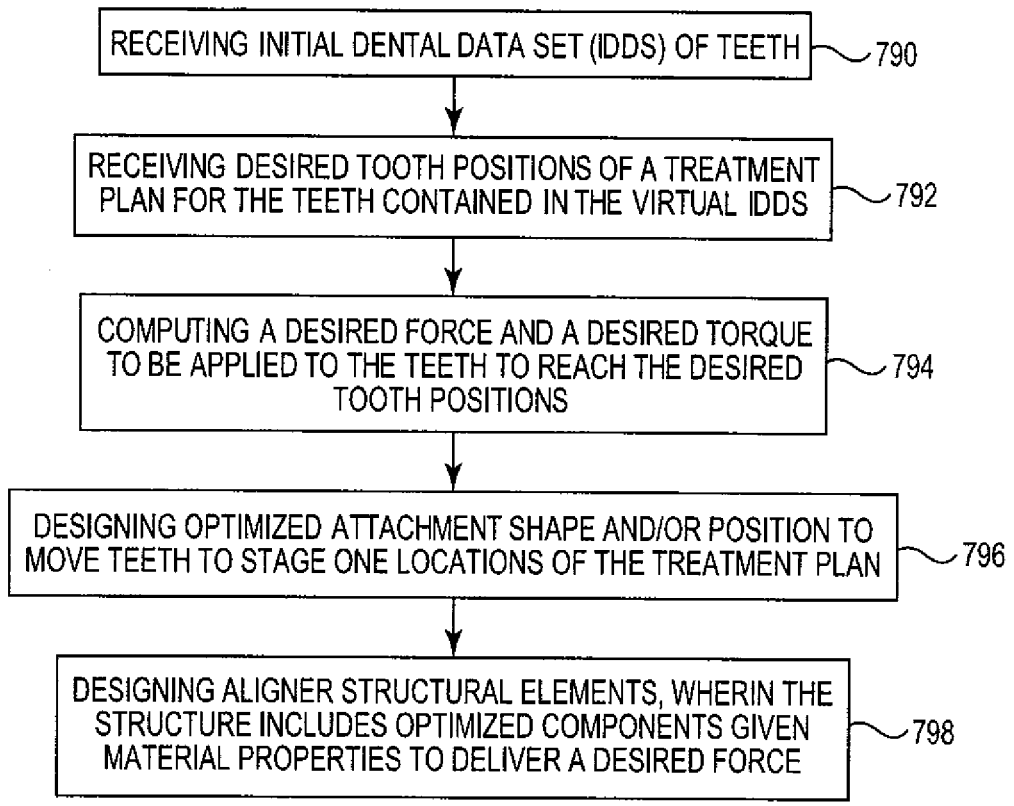
FIG. 7 is a flow chart illustrating a method for identifying force placed on a tooth according to one or more embodiments of the present disclosure.

FIG. 7 is a flow chart illustrating a method for identifying force placed on teeth according to one or more embodiments of the present disclosure. At 790, initial virtual orthodontic data (IOD) of teeth is received.

The IOD may be received in a variety of ways and may contain a variety of information. For example, the IOD can include a gum structure and a mouth bone structure, along with an initial teeth or tooth model.

The patient's teeth may be imaged to obtain digital data using direct and/or indirect structured light, X-rays, three-dimensional X-rays, lasers, destructive scanning, computer-aided tomographic images and/or data, magnetic resonance images, intra-oral scanning technology, photographic reconstruction, and/or other imaging techniques. The IOD can include any portion of the mouth, from an entire mouth tooth arrangement to a single tooth.

A positive model and/or negative impression of the patient's teeth or a tooth may be scanned using an X-ray, laser scanner, destructive scanner, structured light, and/or other scanning system to produce data for the IOD. In some embodiments, the data produced by the scanning system may be converted to other formats to be compatible with the software which is used for manipulating images within the data.

A desired tooth position of a treatment plan for the teeth contained in the virtual IOD is received at 792. The desired position may be the choice of a treatment professional and/or the patient. The desired position can also be a position that has been used for previous patients with similar teeth positioning.

At 794, a desired force and/or torque to be applied to the teeth in order to reach the desired tooth positions is computed. The force and/or torque can be applied using a dental appliance (e.g., appliance, dimple, etc.). Using this desired force and/or torque, a dental appliance can be virtually created using a number of aforementioned creation tools include editing tools to change the shape of the dental appliances or other items related to the movement of the tooth. The dental appliance can be optimally adjusted at 796 until the desired force and torque for moving the tooth from an initial position to the desired position is reached. In some embodiments, an actual force generated by a dental appliance chosen by a patient, treatment professional, and/or other user can be determined. Based on this actual force, an area for the placement of the dental appliance on the tooth can be chosen.

An area for the placement of the dental appliance on the tooth can also be determined without the actual force determination. The desired force and torque to be applied to the tooth can be compared to the determined actual force, and the results can be presented to a user via a user interface.

This can be helpful, for example, by allowing the user to see differences and adjust the shape or position of the dental appliance or other item related to the movement of the tooth. The actual force can be recalculated and/or illustrated to show a revised force of the revised shape and/or position.

For example, the desired position, desired orientation, and/or desired relative magnitude of point contact force can be recomputed with a new constraint if the dental appliance does reach the desired outcome, treatment goal, or model. The dental appliance can also be recreated with a different shape if desired outcomes are not met.

At 798, aligner structural elements are designed including optimized components given material properties to deliver a desired force. Once the forces and/or moments of the forces on the tooth are determined, they can be presented on the user interface (e.g., they can be presented as vector arrows showing direction and/or magnitude of desired force) among other information about the force that may be helpful to the user.

Virtually identifying force placed on a tooth and the dental appliance can be beneficial for many reasons, including the utilization of real world force information, tooth data, and/or other structural data to calculate the position for placement and/or potential shape of a dental appliance or other appliance feature without actually having to test all of these iterations in an actual patient or group of patients. The results can include more accurate movement of teeth, thereby reducing the time of treatment and increasing patient satisfaction, among others.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of computing devices" can refer to one or more computing devices.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A computing device implemented method of virtually identifying force placed on a tooth, comprising:
   receiving initial orthodontic data (IOD) including teeth data;
   creating a virtual set of teeth from the IOD;
   receiving dental appliance information including at least one of dental appliance material properties and characteristics;
   virtually placing a dental appliance, formed from the dental appliance information, onto the virtual set of teeth; and
   computing one or more desired force parameters of a dental appliance based on information from the IOD and dental appliance information to achieve a particular position of a particular segment of a treatment plan; and estimating one or more forces generated by the virtually placed dental appliance as applied to one or more teeth based on information from the IOD and dental appliance information and verifying that the virtually created dental appliance is applying a desired force parameter to the one or more teeth based on a comparison of the desired force and the one or more estimated forces.

2. The method of claim 1, wherein the method includes designing an optimized dental appliance by virtually testing and adjusting the geometry and position of the dental appliance iteratively to reach the desired forces to move teeth to a first stage tooth position based on at least one of the dental appliance material properties, characteristics, and oral cavity characteristics to reach a desired result for moving the teeth to the first stage teeth locations.

3. The method of claim 1, further including displaying the one or more forces applied to one or more teeth and the desired forces via a user interface.

4. The method of claim 1, further comprising comparing one or more desired forces to corresponding estimated forces and presenting the results via a user interface.

5. The method of claim 1, wherein the desired forces and the one or more estimated forces include at least one of: points of contact between teeth and dental appliance, a relative magnitude of point contact force of the dental appliance, an amount of stress on the dental appliance, and individual contacts of the dental appliance.

6. The method of claim 1, wherein the treatment plan has a plurality of dental appliances and wherein the appliances include an aligner and an attachment.

7. The method of claim 1, wherein determining the desired force parameters include data from at least one of: a patient's mouth, typodont data, and scanned dental appliance data.

8. The method of claim 1, wherein the dental appliance material properties and characteristics include thickness of the dental appliance, dimples in the dental appliance, reinforcement structures, and strength of material used to construct the dental appliance.

9. A system for virtually identifying force placed on teeth, comprising:
    a processor;
    memory having instructions executable by the processor to:
    receive initial orthodontic data (IOD) of teeth of a patient;
    identify a virtual target dental model of the teeth based on the IOD representing a treatment plan;
    identify one or more virtually created dental appliances utilized in the treatment plan;
    compute one or more desired force parameters of a dental appliance to achieve a particular position of a particular segment of the treatment plan; and
    estimate forces generated by the virtually created dental appliance as applied to one or more teeth and verify that the virtually created dental appliance is applying a desired force parameter to the one or more teeth based on a comparison of the desired force parameters and the estimated forces.

10. The system of claim 9, wherein the desired force parameters and estimated actual forces present include at least one of a relative magnitude of point contact force of the dental appliance, an amount of stress on the dental appliance, and individual contacts of the dental appliance.

11. The system of claim 10, wherein the relative magnitude of point contact force is displayed on a user interface as force and torque vector arrows showing a direction and magnitude.

12. The system of claim 10, wherein the amount of stress on the dental appliance is displayed on a user interface as a light number of dots to a heavier number of dots scale.

13. The system of claims 10, wherein the individual contacts of the dental appliance are displayed as arrows.

14. The system of claim 9, wherein the estimated forces present on the virtually created dental appliance are displayed on a user interface.

15. The system of claim 9, wherein the system includes a library of data including at least one of: tooth shapes, appliance shapes, appliance characteristics, mounting material characteristics, tooth structures, and mouth structures.

16. A non-transitory computing device memory having executable instructions that can be executed by a processor to cause a computing device to perform a method of virtually identifying force placed on a tooth, comprising:
    receiving initial orthodontic data (IOD) of teeth;
    receiving desired tooth positions of a treatment plan for the teeth contained in the IOD;
    computing a desired force and a desired torque to be applied to the teeth to reach the desired tooth positions;
    computing an estimated force and estimated torque generated by a virtually placed dental appliance as applied to one or more teeth based on information from the IOD and dental appliance material and appliance characteristic information and verifying the virtual dental appliance is applying a desired force parameter to the one or more teeth; and
    designing an optimized dental appliance shape and position to move teeth to the desired tooth positions based on a comparison of the desired force and torque and the estimated force and torque.

17. The memory of claim 16, wherein designing the optimized dental appliance shape and position includes:
    virtually testing and adjusting the dental appliance iteratively to attempt to reach the desired force and torque for moving a particular tooth from an initial position to a desired position based on the comparison.

18. The memory of claim 17, further including:
    displaying the desired force and desired torque via a user interface; and
    displaying the estimated force and torque applied to the teeth by the dental appliance via the user interface.

19. The memory of claim 17, wherein one of: position, shape, and orientation of the dental appliance are modified by the user via the user interface if the desired force and torque are not obtained.

20. The memory of claim 16, wherein a new one of: position, shape, and orientation is calculated and suggested to the user via the user interface.

* * * * *